(12) United States Patent
Sharma et al.

(10) Patent No.: US 11,980,566 B2
(45) Date of Patent: May 14, 2024

(54) DELIVERY SYSTEM FOR FECAL MANAGEMENT DEVICE

(71) Applicant: CM Technologies, Inc., San Diego, CA (US)

(72) Inventors: Amit Kumar Sharma, New Delhi (IN); Nishith Chasmawala, Surat (IN); Shreyas Uday Dighe, Nagpur (IN)

(73) Assignee: CM Technologies, Inc., San Diego, CA (US)

( * ) Notice: Subject to any disclaimer, the term of this patent is extended or adjusted under 35 U.S.C. 154(b) by 159 days.

(21) Appl. No.: 17/424,922

(22) PCT Filed: Jan. 22, 2020

(86) PCT No.: PCT/IB2020/050487
§ 371 (c)(1),
(2) Date: Jul. 22, 2021

(87) PCT Pub. No.: WO2020/152595
PCT Pub. Date: Jul. 30, 2020

(65) Prior Publication Data
US 2022/0104963 A1 Apr. 7, 2022

Related U.S. Application Data

(60) Provisional application No. 62/795,036, filed on Jan. 22, 2019.

(51) Int. Cl.
*A61F 5/451* (2006.01)
*A61M 25/04* (2006.01)

(52) U.S. Cl.
CPC ............ *A61F 5/451* (2013.01); *A61M 25/04* (2013.01); *A61M 2202/068* (2013.01)

(58) Field of Classification Search
CPC ..... A61F 5/451; A61B 10/0038; A61M 25/04
See application file for complete search history.

(56) References Cited

U.S. PATENT DOCUMENTS

2015/0011955 A1   1/2015 Sharma et al.

FOREIGN PATENT DOCUMENTS

KR    102110052 B1 * 11/2018  ............. A61F 5/442
WO    2011139498 A1    11/2011

OTHER PUBLICATIONS

International Search Report from PCT International Application No. PCT/IB2020/050487, dated May 27, 2020.

* cited by examiner

*Primary Examiner* — Philip R Wiest
*Assistant Examiner* — Matthew Wrubleski
(74) *Attorney, Agent, or Firm* — Budzyn IP Law, LLC

(57) ABSTRACT

The invention provides an apparatus for fecal management, comprising a device for collection of fecal discharge, and an insertion component. The device for collection of fecal discharge may comprise an expansile retaining component configured for deployment within a subject's rectum and having an annular cross-section. The insertion component may be configured for rectal insertion of the retaining component, and may include an elongate shaft having a first end positioned proximal to the retaining component and a second end positioned distal to the retaining component. At least one of the retaining component and the elongate shaft may be provided with a plurality of constraining members configured to releasably constrain the retaining component in a collapsed configuration against an external surface of the elongate shaft.

11 Claims, 22 Drawing Sheets

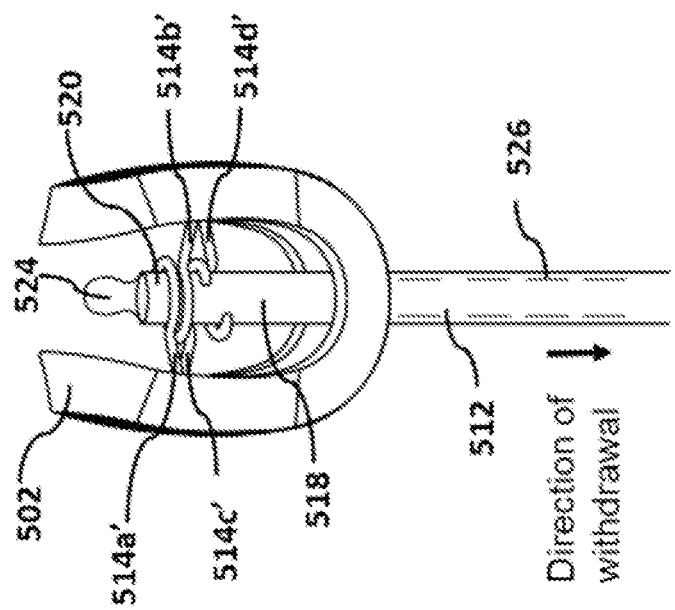

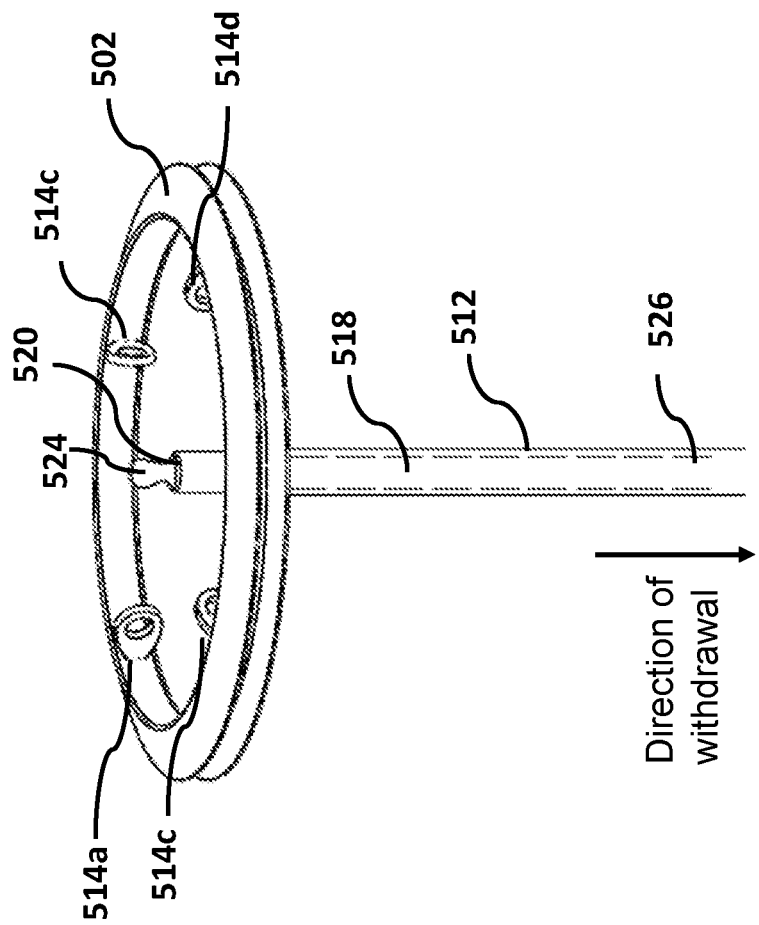

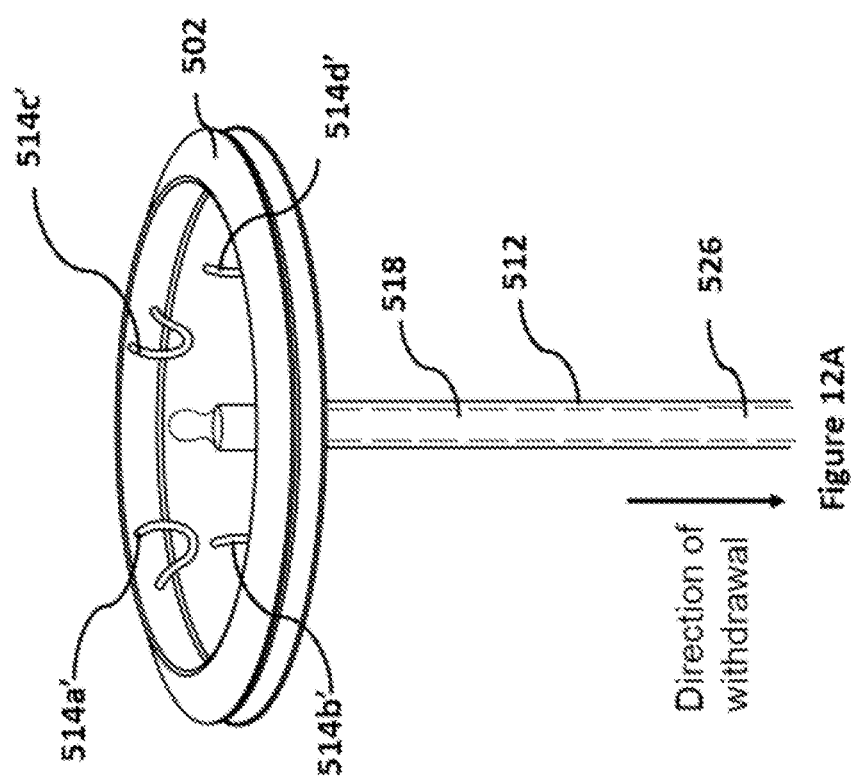

DELIVERY SYSTEM FOR FECAL MANAGEMENT DEVICE

CROSS-REFERENCE TO RELATED APPLICATIONS

This Application is a National Stage Application under 35 U.S.C. § 371 of PCT Application No. PCT/IB2020/050487, filed Jan. 22, 2020, which claims priority from and the benefit of US Provisional Patent Application No. 62/795,036 filed Jan. 22, 2019, which are hereby incorporated by reference in their respective entireties.

FIELD OF THE INVENTION

The invention relates to the domain of stool collection, and provides devices for collection of stool or fecal discharge and delivery systems therefor.

BACKGROUND

The present invention relates to solutions for containment or management of fecal output.

Options for containment or management of fecal output known in the art include absorbent pads in the form of diapers or sanitary napkins, anal plugs, fecal collectors in the form of collection bags or pouches, and indwelling catheters.

Of the various available solutions, indwelling catheters provide a promising solution for managing fecal incontinence. An indwelling catheter is placed inside the rectum and an expansible retaining member comprising a self-expanding resilient ring or an inflatable balloon or cuff is used to hold the catheter inside the rectum. The retaining member is delivered in a compressed state into the rectum through the anal opening, and is allowed to, or caused to expand within the rectum. The retaining member also provides an annular lumen to allow passage of stool. The retaining member is connected to a collection bag, for feces.

It has however been found that delivery of an indwelling catheter or indwelling component into the rectum presents certain challenges. One solution is to compress the retaining member and deliver and position the retaining member within a subject's rectum manually. This method necessarily requires a trained healthcare provider, and involves digit based manipulation of the indwelling component within the subject's rectum—which has been found to provide a poor user experience for both the patient and healthcare provider.

Other solutions involve a variety of insertion devices—which involves introducing the expansible retaining member into the subject's rectum through the anal opening using an obdurator type delivery device that includes at least a restraining outer sheath disposed around the expansible retaining member—and which holds the expansible retaining member in a compressed configuration. A tip or front portion of the obdurator type delivery device (or the restraining outer sheath) is inserted into the anal opening, and the compressed retaining member may thereafter be deployed within the rectum by removing the retaining member from the constraining influence of the restraining outer sheath.

Such deployment may be achieved in a variety of ways, including (i) by operation of a plunger disposed co-axially within the restraining outer sheath and which may be used to eject or push the compressed retaining member out of the restraining outer sheath, (ii) by using a frangible, disintegrable or dismantle-able restraining outer sheath having a plurality of segments that may be manipulated in a manner so that the plurality of segments partially or wholly separate from each other within the rectum—thereby freeing the compressed retaining member from the constraining influence of said restraining outer sheath, and allowing the retaining member to expand within the rectum, or (iii) by using a restraining outer sheath that can be withdrawn from the subject's rectum without simultaneously withdrawing the retaining member—thereby freeing the compressed retaining member from the constraining influence of said restraining outer sheath, and allowing the retaining member to expand within the rectum.

All of these solutions have been found to be bulky and uncomfortable from a patient's perspective, as the diameter of restraining outer sheath is typically greater than the diameter of the retaining member by itself when in a compressed configuration, and further in view that the sensation of insertion and withdrawal of the restraining outer sheath has been found to significantly increase patient discomfort—as a result of the larger delivery profile.

Additionally, it has been found that complications involved in removing the restraining outer sheath (while ensuring that the retaining member is properly deployed within the rectum) increases the level of complexity in connection with use of such devices, insofar as healthcare providers are concerned. It has also been found that retraction of the restraining outer sheath with controlled movement is not always possible—resulting in uneven withdrawal or inadvertent jerking back of the restraining outer sheath and consequent improper positioning of the retaining member as well as unnecessary trauma or sensation to the patient.

The use of a restraining outer sheath as a delivery mechanism for the expansible retaining member has also been found to permanently damage or deform the expansible retaining member—by causing a deterioration in resilience/expansibility or a permanent deformation of shape of the expansible retaining member, as a result of the expansible retaining member being constrained within the restraining outer sheath for long periods of time.

There is accordingly a need for a delivery system that presents a substantially smaller profile and which enables convenient deployment of an expansible retaining member of an indwelling catheter type fecal management system.

SUMMARY

The invention relates to the domain of stool collection, and provides devices for collection of stool or fecal discharge and delivery systems therefor.

The invention provides an apparatus for fecal management, comprising a device for collection of fecal discharge, and an insertion component.

The device for collection of fecal discharge may comprise an expansile retaining component configured for deployment within a subject's rectum and having an annular cross-section, said annular cross-section of the retaining component forming a fluid inlet into an open end of a collection component affixed to said retaining component and forming a receptacle for matter discharged from a subject's rectum.

The insertion component may be configured for rectal insertion of the retaining component, said insertion component comprising an elongate shaft having a first end positioned proximal to the retaining component and a second end positioned distal to the retaining component.

At least one of the retaining component and the elongate shaft may be provided with a plurality of constraining members configured to releasably constrain the retaining component in a collapsed configuration against an external surface of the elongate shaft.

The apparatus may be configured such that responsive to release of the elongate shaft from engagement with the retaining component, expansile properties of the retaining component urge the retaining component into an expanded annular configuration.

In an embodiment of the invention, the plurality of constraining members are located on the retaining component. Further, each of the plurality of constraining members may comprise a fastening collar having an aperture provided therethrough, wherein said aperture is configured to permit a segment of the elongate shaft to be withdrawably positioned within said fastening collar.

The plurality of fastening collars may be located along a periphery of the retaining component, such that aligning the apertures that respectively correspond to each constraining member vertically around a single longitudinal axis forces the retaining component into a collapsed configuration.

The elongate shaft may be withdrawably positioned within the apertures corresponding to the plurality of constraining members to hold the plurality of constraining members in a configuration wherein said apertures are vertically aligned around a single longitudinal axis.

In an embodiment of the apparatus, an external diameter of the elongate shaft at a portion that is in releasable engagement with the retaining component, is less than an external diameter of the retaining component in the collapsed configuration.

The plurality of constraining members may be located on the elongate shaft and may be configured to releasably retain the retaining component in a collapsed configuration against the external surface of the elongate shaft.

In an apparatus embodiment, one of the elongate shaft and the retaining component are provided with a first set of reciprocal constraining members that releasably engage with a second set of reciprocal constraining members on the other of the elongate shaft and the retaining component to releasably retain the retaining component in a collapsed configuration against the external peripheral surface of the elongate shaft.

In an apparatus embodiment, the elongate shaft is releasable from engagement with the retaining component by withdrawal of the second end of said elongate shaft in a direction distal to the retaining component.

In a particular embodiment, the first end of said elongate shaft is provided with a protrusion that prevents inadvertent release of engagement between the elongate shaft and the retaining component.

The invention additionally provides a kit for fecal management, comprising (i) a device for collection of fecal discharge comprising an expansile retaining component configured for deployment within a subject's rectum and having an annular cross-section, said annular cross-section of the retaining component forming a fluid inlet into an open end of a collection component affixed to said retaining component and forming a receptacle for matter discharged from a subject's rectum, and (ii) an insertion component for rectal insertion of the retaining component, said insertion component comprising an elongate shaft having a first end configured for positioning proximal to the retaining component and a second end configured for positioning distal to the retaining component—wherein at least one of the retaining component and the elongate shaft are provided with a plurality of constraining members configured to releasably constrain the retaining component in a collapsed configuration against an external surface of the elongate shaft.

BRIEF DESCRIPTION OF THE ACCOMPANYING DRAWINGS

FIGS. 9 to 15C illustrate different components of the insertion component and the manner in which said components enable the insertion component to restrain the retaining component in a compressed configuration, and to selectively release the retaining component to enable said retaining component to transition to an expanded configuration.

DETAILED DESCRIPTION

Figure 1A:
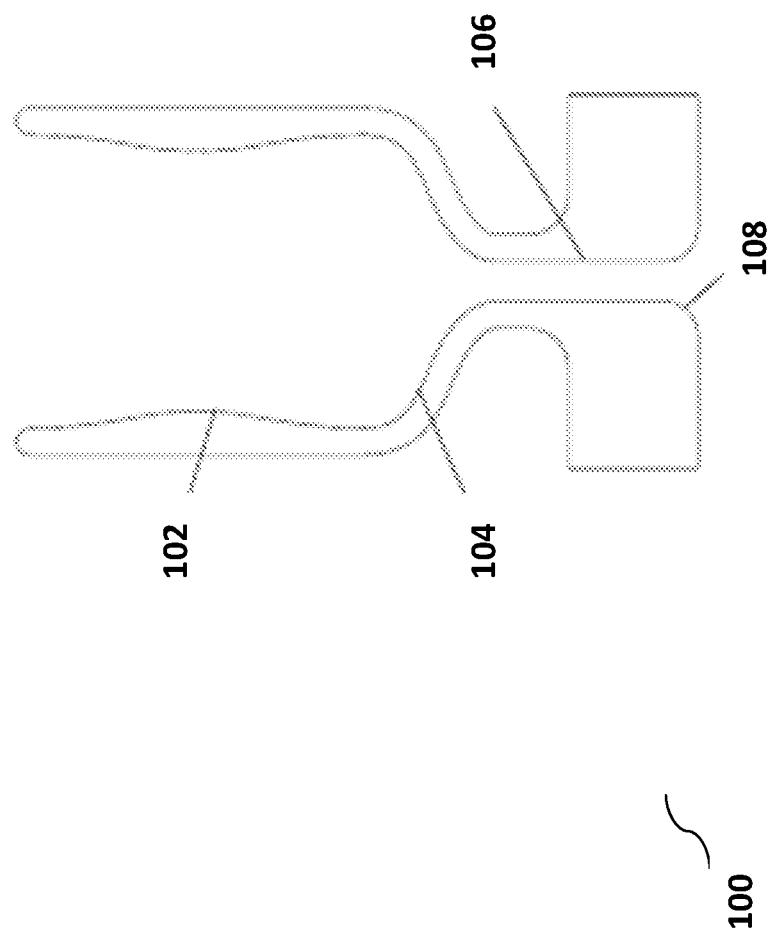
FIGS. 1A and 1B illustrate portions of human rectal anatomy.

The invention comprises a delivery system for an indwelling component based device for fecal output management.

The device for fecal output management is a device configured for collection of fecal discharge, and includes a retaining component for retaining a part of the device within the rectum, coupled with a collection component for collecting stool or liquid discharge received from the rectum. The device may additionally include a fluid delivery component to enable delivery of fluid to the colon, and/or a withdrawal component to support safe removal of the device from the patient.

The invention specifically includes an insertion component to constrain the retaining component in a collapsed state during placement into the rectum.

For the purposes of the description below, the term "proximal end" (wherever used in connection with an object or component) shall be understood as being an end of said object or component that is closer to a subject's rectum (or the end which is inserted into a subject's anal opening) and the term "distal end" (wherever used in connection with an object or component) shall be understood as being an end of said object or component that is further from a subject's rectum (or the end which is not inserted into a subject's anal opening).

As described in more detail below, the retaining component may comprise a flexible, resilient and expansible substantially "ring-like" structure defining a lumen or passage within the periphery thereof. The retaining component is caused by its resilient properties to naturally expand from a collapsed state having a small cross sectional area to an expanded state having a larger cross sectional area. The resilient properties of the retaining component ensures that in an expanded configuration the retaining component presses against the rectal walls, causing the external peripheral surface(s) of the retaining component to resiliently conform to adjacent rectal walls and to ensure that a complete seal is created between the external periphery of the retaining component and the rectal walls—thereby ensuring that any stool or fecal discharge passes through the lumen of the retaining component instead of leaking through spaces between the external periphery and adjacent rectal walls.

The collection component (or transit sheath) comprises a bag, chute or tube made of a thin, low-friction, flexible, skin friendly material that has an open first end through which stool or fluid may enter said collection component. The first end of the collection component may be coupled with the retaining component such that stool or liquid discharge entering the lumen of the retaining component passes into the collection component through the open proximal end of said collection component. The collection component may be configured to hold and contain material that passes into it through the open proximal end. The other end of the collection component may in an embodiment be a closed end, so as to ensure that the stool or liquid discharge is retained within the collection component.

The insertion component according to the present invention is in an embodiment, an insertion device used to deliver the retaining component into a subject's rectum (in the compressed state), and the retaining component is thereafter released from the constraints imposed by the insertion component—thereby permitting it to transition to an expanded state. The insertion component is subsequently withdrawn from the rectum, while the expanded retaining component remains within the subject's rectum. Since the retaining component is coupled to the collection component, stool or fluid discharge from the rectum entering the retaining component transits into the collection component, which is at least partially positioned outside the rectum.

The fluid delivery component comprises an assembly configured to deliver fluid from an external source to the subject's rectum while the retaining component is positioned within the rectum. The fluid delivery component comprises a fluid conduit having an open proximal end, a distal end and a lumen connecting the two—and may in an embodiment comprise a length of tubing or piping of appropriate diameter. The fluid delivery component may be coupled with one or both of the retaining component and the collection component such that when the retaining component is positioned within a subject's rectum, the open proximal end is positioned within the subject's colon while the distal end lies outside of the rectum. The lumen connecting the two ends provides a fluid passageway that enables fluid to be delivered from the distal end through the open proximal end and to the subject's colon. As a result of the configuration, the fluid delivery component enables delivery of enema fluid or other fluid into the subject's rectum once the retaining component has been positioned within the rectum.

The withdrawal component comprises a structure or assembly that is configured to change either or both of the orientation and/or cross-section of the retaining component to enable withdrawal of the retaining component from the rectum. In an embodiment discussed in this invention the withdrawal component and the fluid delivery component may comprise a single component.

Specific embodiments of the above are discussed in greater detail below.

Figure 1B:
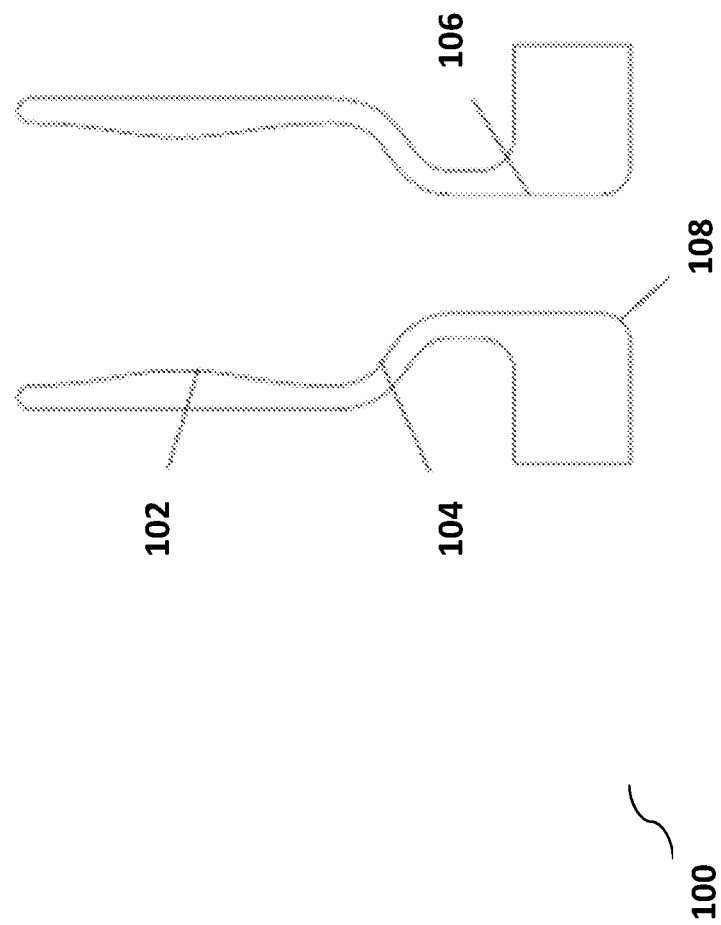

FIG. 1A illustrates the relevant portions of the human rectum 100, including rectal walls 102, the anorectal junction 104, the anal canal 106, and the anal verge 108. In FIG. 1A, anal canal 106 is shown in a constricted position. FIG. 1B depicts the same portions of the rectal anatomy but with the anal canal 106 now in an expanded position (for example when the subject is passing stool).

Figure 2A:
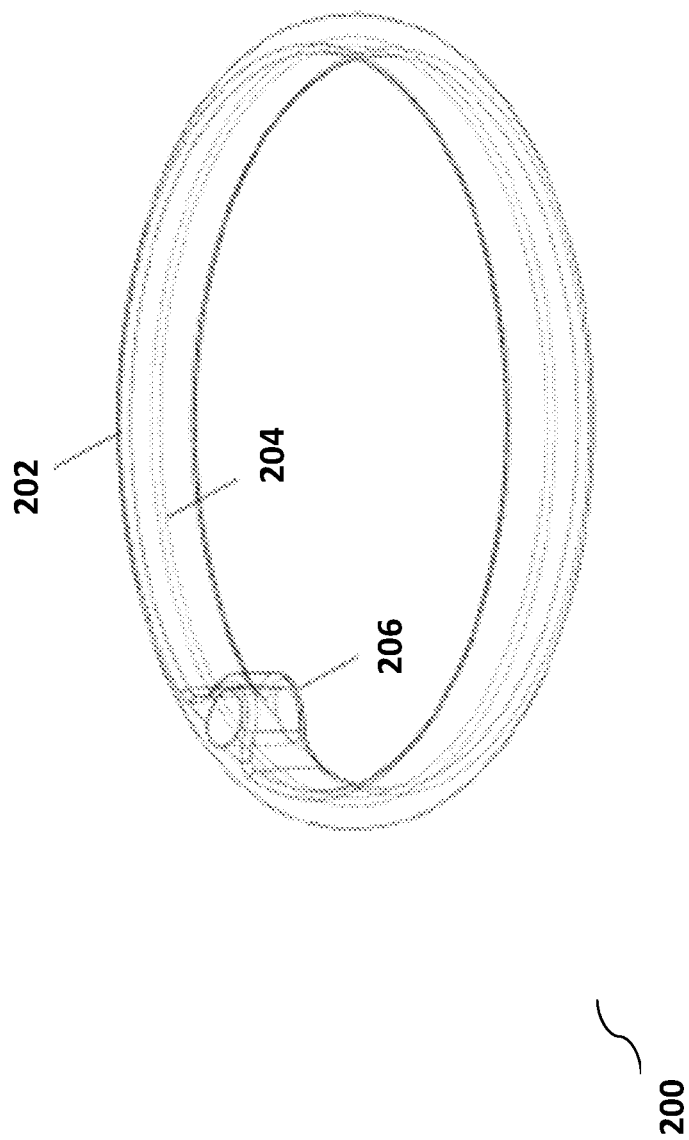
FIG. 2A illustrates an embodiment of a retaining component in an expanded state in accordance with the present invention.

FIG. 2A illustrates an embodiment of the retaining component 200 in an expanded state. Retaining component 200 comprises a pliant and collapsible annular body 202 comprising a first material and a resilient ring 204 comprising a second material, with resilient ring 204 embedded within said annular body 202. Annular body 202 may additionally include a port (or retaining cavity) 206 for housing or holding an end of the fluid delivery component.

Owing to the fact that it is comprised of collapsible annular body 202 and a resilient ring 204 embedded therewithin, retaining component 200 can be collapsed into a number of different configurations to reduce its cross-sectional profile for the purposes of delivering it into a subject's rectum.

Figure 2B:
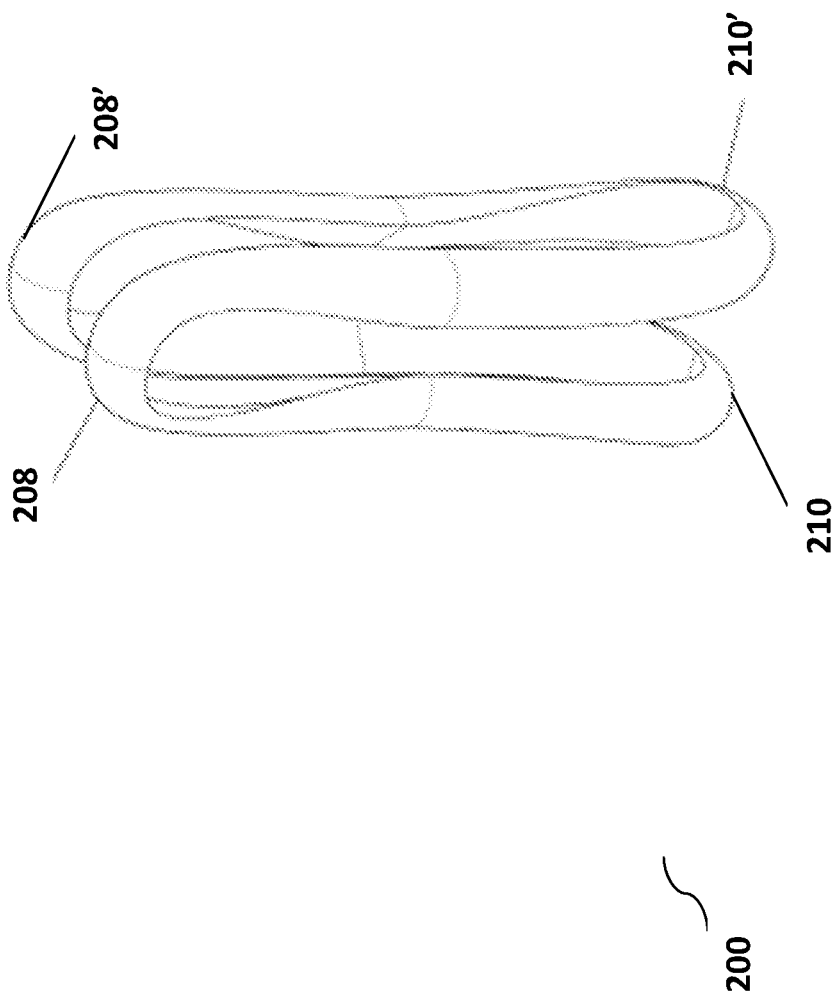
FIGS. 2B and 2C illustrate configurations in which the retaining component may be collapsed.

FIG. 2B illustrates a first exemplary configuration into which retaining component 200 can be collapsed—wherein in said collapsed state, retaining component 200 has been compressed and collapsed along two mutually perpendicular axes to form two peaks 208, 208' and two troughs 210, 210'.

Figure 2C:
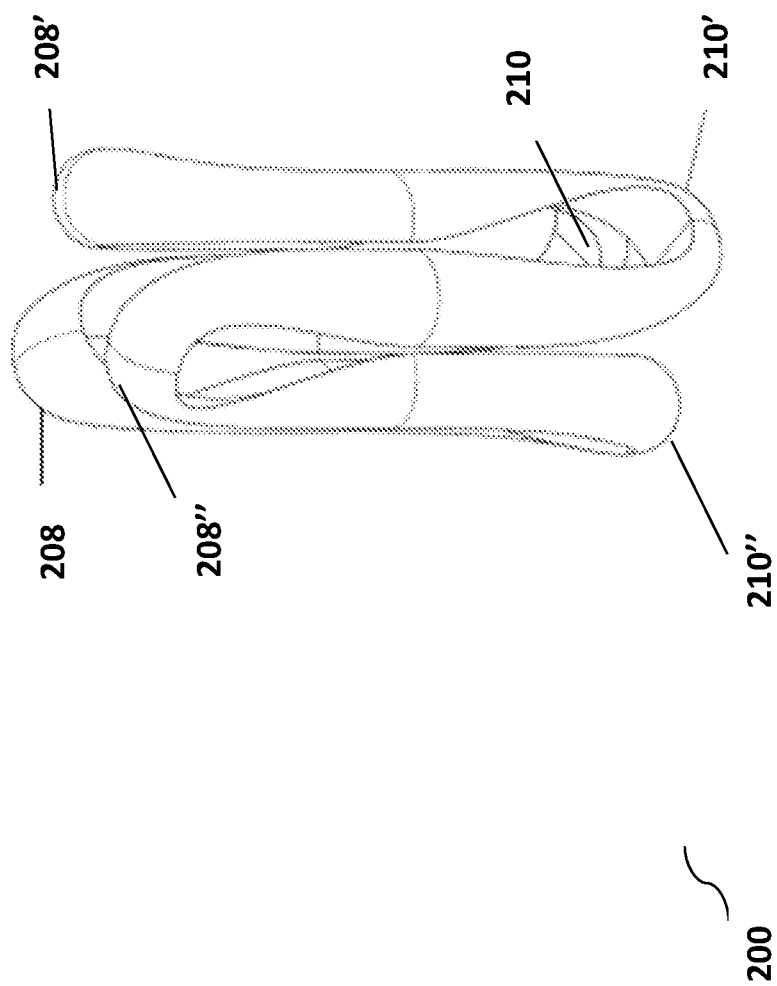

FIG. 2C illustrates a second exemplary configuration into which retaining component 200 can be collapsed—wherein in said collapsed state, retaining component 200 has been compressed and collapsed along three axes, each arranged with 120 degrees between them, to form three peaks 208, 208', 208" and three troughs 210, 210', 210".

It would be understood that the embodiments of FIGS. 2B and 2C are only exemplary and that retaining component 200 can be collapsed into any number of other compressed configurations. However, it will be noted by comparing the embodiments of FIGS. 2B and 2C to the illustrated embodiment in FIG. 2A, that in its collapsed state, the cross-sectional profile of retaining component 200 is substantially reduced—enabling convenient insertion into and withdrawal from a subject's rectum.

Figure 3:
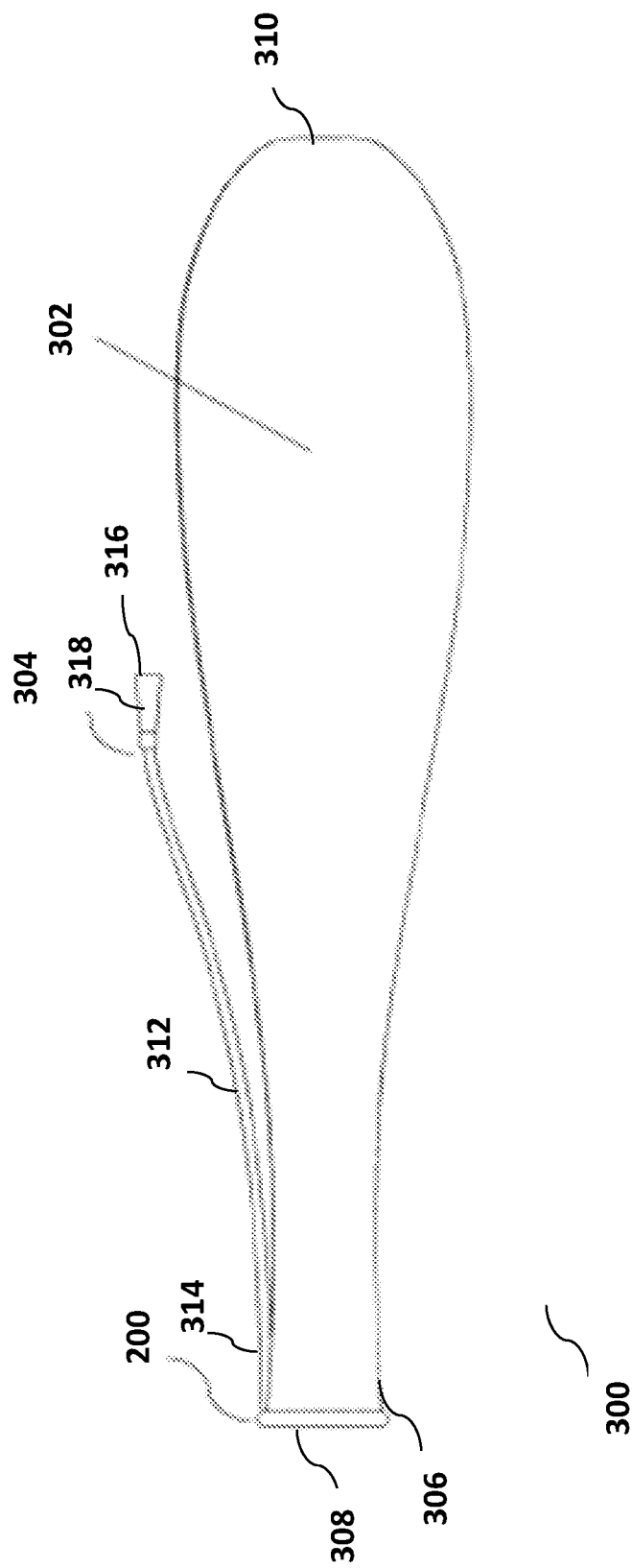
FIG. 3 illustrates an assembled device for collection of fecal discharge in accordance with embodiments of the present invention.

FIG. 3 illustrates an assembled device 300 for collection of fecal discharge, said device 300 comprising retaining component 200 for retaining a part of the device within the rectum, coupled with a collection component 302 for collecting stool or liquid discharge received from the rectum, and a fluid delivery component 304 for delivery of fluid to the colon. In the illustrated embodiment, and as discussed in further detail below, the fluid delivery component 304 may also act as a withdrawal component to support safe removal of the device 300 from a patient's rectum.

As illustrated in FIG. 3, collection component 302 comprises a bag (or alternatively a chute or tube) made of a thin, low-friction, flexible, skin friendly material that has an open first end 306 through which stool or fluid may enter said collection component 302. The open first end of collection component 302 may be coupled with retaining component 200 such that stool or liquid discharge entering an annular opening 308 formed by the retaining component 200, passes into the collection component 302 through first open end 306 of said collection component 302. The collection component 302 may be configured to hold and contain material that passes into it through the open proximal end. In an embodiment, this is achieved by ensuring that a second end 310 of collection component 302 is a closed end.

Also shown in FIG. 3 is fluid delivery component 304—which comprises an assembly configured to deliver fluid from an external source to the subject's rectum while the retaining component 200 is positioned within the rectum. Fluid delivery component 304 comprises a fluid conduit 312 having a first open end 314 positioned proximal to retaining component 200 and a second open end 316 positioned distal to retaining component 200. As shown in FIG. 3, second open end 316 of fluid delivery component 304 may include a connector 318, which enables fluid delivery component 304 to be connected to a fluid source. Fluid from the fluid source may enter second open end 316, pass through fluid conduit 312 and be delivered into a subject's rectum through first open end 314 of fluid conduit 312. Referring back to FIG. 2A, in an embodiment of the invention, fluid conduit 312 or first open end 314 of said fluid conduit 312 may be housed or held within port (or retaining cavity) 206 of retaining component 200—which ensures that when retaining component 200 is disposed within a subject's rectum, first open end 314 of fluid conduit 312 is also disposed within the subject's rectum, thereby enabling fluid to be delivered to the subject's rectum or colon through fluid delivery component 304.

Figure 4:
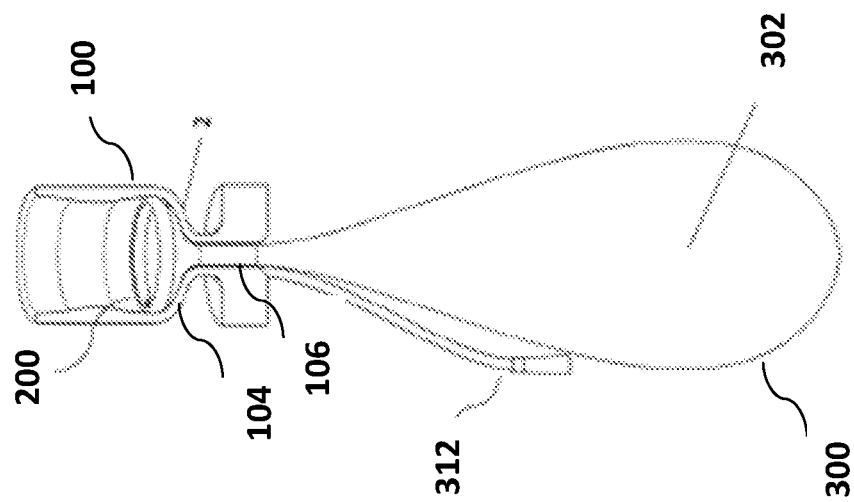
FIG. 4 illustrates an exemplary instance of a device for collection of fecal discharge, positioned within a patient's rectum.

FIG. 4 illustrate an exemplary instance of device 300 for collection of fecal discharge positioned within a patient's rectum 100. As shown in FIG. 4, retaining component 200 is positioned within the subject's rectum 100 above the shelf structure formed by the subject's anorectal junction 104. Owing to the distance between the walls of the rectum 100 above the anorectal junction 104, retaining component 200 has transitioned to its expanded state, and in its expanded state rests securely on the walls of the anorectal junction 104. Since the distance between the walls of the anal canal 106 beneath the anorectal junction are narrower than the expanded cross section of retaining component 200 in its expanded state, retaining component 200 is securely held by anorectal junction 104 and accidental withdrawal of retaining component 200 from the subject's rectum is prevented.

It would be understood that retaining component 200 may be delivered to a position above the anorectal junction 104 by compressing retaining component 200 into a configuration having a cross-section less than the cross-section of anal canal 106, delivering said retaining component 200 (while remaining in a compressed configuration) through anal canal 106 to a position above anorectal junction 104, and thereafter releasing retaining component 200 from the applied compressive forces—thereby allowing retaining component 200 to transition to its expanded state, in which expanded state, it naturally resists withdrawal through the narrower anal canal 106.

As shown in FIG. 4, first ends of collection component 302 and fluid delivery component 304 (each of which have an end affixed to or in proximity to retaining component 200), respectively trail said retaining component 200 into the rectum, while opposite ends of said collection component 302 and fluid delivery component 304 pass through anal canal 106 and are located outside of rectum 100.

As in the case of insertion, removal of retaining component 200 (and consequently of device 300) from a subject's rectum requires application of forces that cause the retaining component 200 to transition from an expanded state to a compressed state having an orientation or cross-section sufficient to enable retaining component 200 to be withdrawn through anal canal 106 by application of withdrawing force. In an embodiment, retaining component 200 may be caused to change orientation or collapse into a sufficiently compressed state to enable withdrawal through anal canal 106 by application of (i) withdrawing force (in a direction distal to the rectum) at a plurality of points distributed around a periphery of retaining component 200 (which withdrawing force may be applied by one or more tethers provided on the periphery of retaining component 200)—which causes retaining component 200 to collapse or transition to a collapsed state, whereinafter continued application of withdrawing force in a direction distal to the rectum causes retaining component 200 (and device 300 as a whole) to be withdrawn from the subject's rectum.

The invention provides an insertion component for the above described indwelling component/expansible retaining component based device for fecal output management. The insertion component includes an elongate shaft including a proximal end, a distal end, and a retaining component constraining segment located between the proximal end and the distal end. Insofar as the elongate shaft is concerned, the term "proximal end" shall be understood as being an end closer to a subject's rectum (or the end which is inserted into a subject's anal opening) and the term "distal end" shall be understood as being an end further from a subject's rectum (or the end which is not inserted into a subject's anal opening).

As will be discussed in more detail hereinbelow, the insertion component is used to deliver the retaining component into a subject's rectum while in a collapsed (or compressed) configuration and subsequently allow transition to an expanded (or open) configuration. At least one of the retaining component and/or the elongate shaft are provided with one or more constraining members that utilize the constraining segment of the elongate shaft to hold the retaining component in a collapsed configuration. The one or more constraining members are configured to respond to manipulation in a way that permits the retaining component to be released and assume its expanded configuration.

Figure 5:
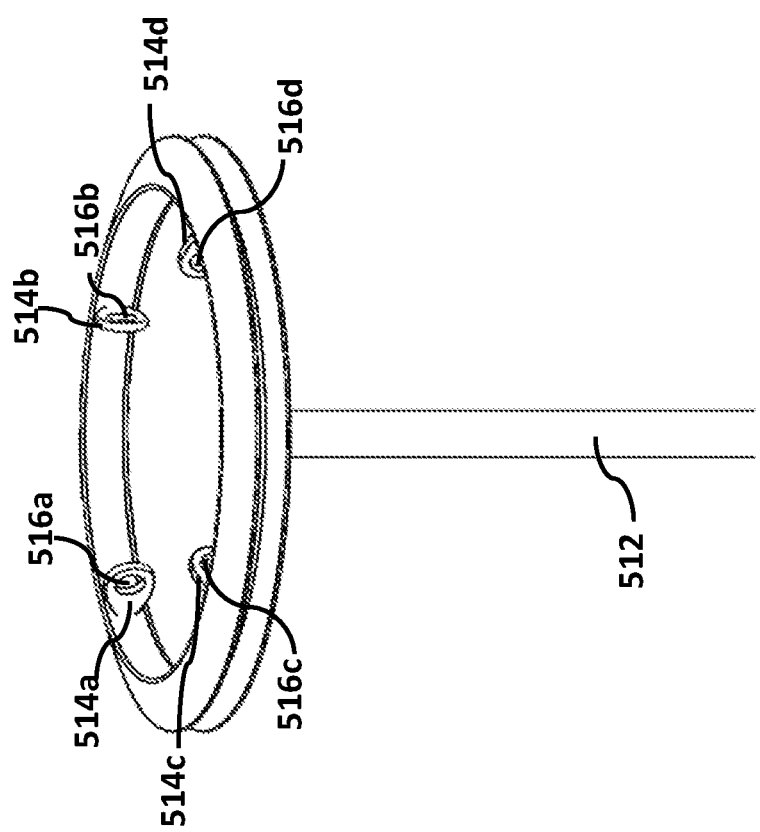
FIGS. 5 to 8 illustrate a first embodiment of a delivery system comprising an insertion component and a retaining component that is delivered to a subject' rectum through action of the insertion component in accordance with the present invention.

FIG. 5 illustrates an embodiment of the retaining component 502 of the device for fecal output management having a plurality of constraining members 514a to 514d positioned at discrete points along an internal periphery of retaining component 502. Each constraining member 514a to 514d comprises a fastening collar or fastening ring having a corresponding aperture 516a to 516d provided therethrough, wherein each fastening collar or fastening ring is affixed to retaining component 502.

Retaining component 502 may optionally have affixed thereto a hollow tubular extrusion 512 having an open first end proximal to retaining component 502 and an open second end distal to said retaining component 502, and an internal lumen connecting the two open ends. In an embodiment said tubular extrusion may be sized to allow the elongate shaft of the insertion component to pass therethrough. In an embodiment of the invention, the hollow tubular extrusion 512 affixed to retaining component 502 may comprise a fluid conduit 312 of the type discussed previously in connection with FIG. 3.

Figure 6:
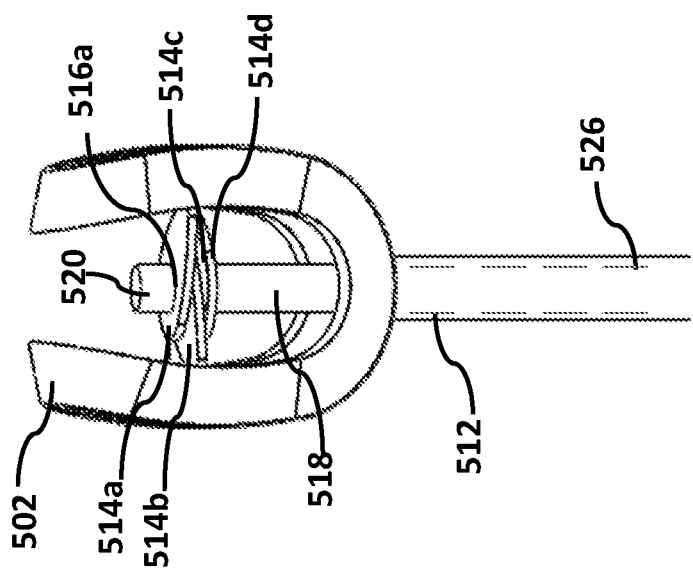

As shown in FIG. 6, the plurality of constraining members 514a to 514d may be sized and located such that when retaining component 502 is in a collapsed configuration, the respective apertures 516a to 516d of constraining members 514a to 514d are substantially aligned so as to permit elongate shaft 518 of the insertion component to pass through all of said apertures. As a result of the elongate shaft 518 threading the respective apertures 516a to 516d of constraining members 514a to 514d, said constraining members are affixed to elongate shaft 518—thereby holding retaining component 502 in a collapsed configuration about or against elongate shaft 518.

In the embodiment shown in FIG. 6, elongate shaft 518 is positioned within hollow tubular extrusion 512 such that a proximal end 520 of said elongate shaft 518 emerges from an open first end of said hollow tubular extrusion 512 that is proximal to retaining component 502 and is threaded through apertures 516a to 516d of constraining members 514a to 514d.

Figure 7:
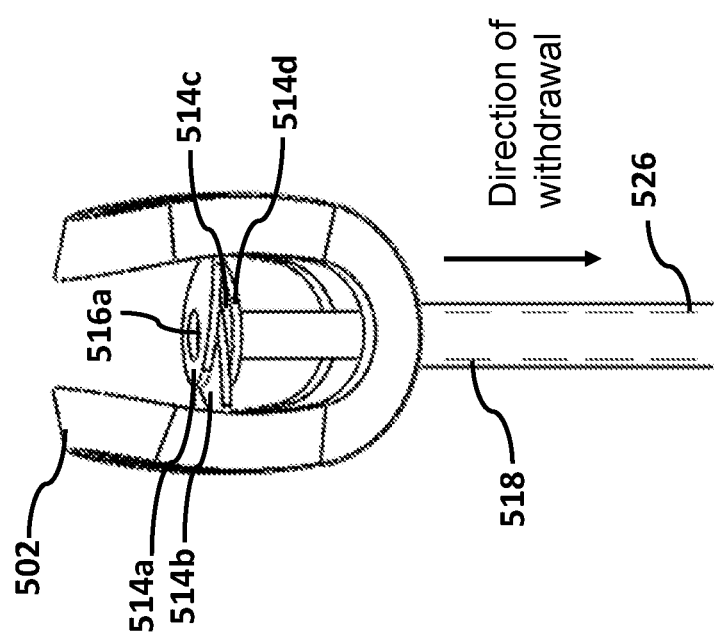

As shown in FIG. 7, elongate shaft 512 may be withdrawn outward through the open second end of said hollow tubular extrusion 512 that is distal to retaining component 502—thereby resulting in the proximal end of said elongate shaft 512 being withdrawn from apertures 516a to 516d of constraining members 514a to 514d. Upon withdrawal of elongate shaft 512 from the apertures 516a to 516d of constraining members 514a to 514d, said constraining members are released from their engagement with elongate shaft 512—as a result of which the expansile properties of retaining component 502 allows said retaining component to transition from the collapsed configuration, illustrated in FIGS. 6 and 7, towards the expanded configuration shown in FIG. 8.

Figure 8:
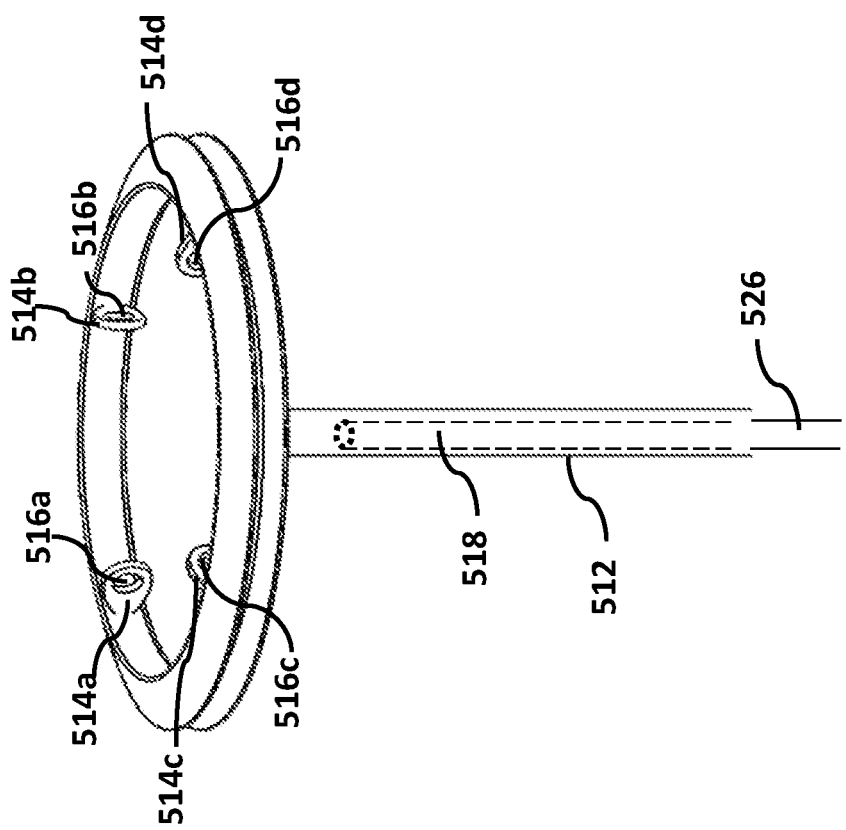

The above explanation in connection with FIGS. 6 to 8 establishes that the configuration shown in FIG. 6 (wherein retaining component 502 of the device for fecal output management is held in a constrained or collapsed configuration by elongate shaft 518) may be used for delivering said retaining component into a subject's rectum. Said delivery may be achieved by inserting said retaining component 502 in its collapsed configuration through the anal opening and into the rectum by placing the collapsed retaining component 502 and proximal end of elongate shaft 518 at the anal opening and applying pressure to the distal end of elongate shaft 518 in the direction of the anal opening—thereby causing collapsed retaining component 502 and the proximal end of elongate shaft 518 to enter the subject's rectum. Thereafter, distal end of elongate shaft 518 is manipulated to release collapsed retaining component 502 from its engagement with elongate shaft 518, and permitting said retaining component to assume its expanded configuration within the subject's rectum, while the elongate shaft 518 is withdrawn from the subject's rectum through the anal opening.

While in the embodiment illustrated in FIGS. 6 to 8, constraining members 514a to 514d are provided on an inner periphery of retaining component 502, it will be understood that constraining members 514a to 514d may be located on an outer periphery of retaining component 502, or some constraining members 514a to 514d may be located on an inner periphery while others are located on the outer periphery.

The number of constraining members, their type and their location on retaining component 502 and/or on elongate shaft 518 may be varied or selected according to a collapsed configuration that is intended for retaining component 502 when it is releasably constrained against elongate shaft 518. In various embodiments or configurations, such as those illustrated in FIGS. 2B and 2C, the number of constraining members, their type and location may be selected so that retaining component 502 is releasably constrained against elongate shaft 518 in a desired compressed configuration.

While FIGS. 6 to 8 illustrate constraining members on the retaining component 502 that are designed to releasably fasten said retaining component 502 to elongate shaft 518 in a collapsed configuration, said constraining members may alternatively be positioned on elongate shaft 518 and may be designed to releasably fasten said elongate shaft 518 and retaining component 502 together. In yet other embodiments, each of elongate shaft 518 and retaining component 502 are provided with fasteners or constraining members that are configured to cooperatively engage with fasteners or constraining members on the other of elongate shaft 518 and retaining component 502 so as to ensure that retaining component 502 is releasably constrained against elongate shaft 518 in a collapsed configuration, and in a manner that enables release thereof by manipulation of a distal end of elongate shaft 502.

It would also be understood that constraining members 514a to 514d and elongate shaft 518 may include a variety of different types of mechanisms to ensure that retaining component 502 is releasably but securely engaged in its collapsed configuration with elongate shaft 518.

Figure 9:
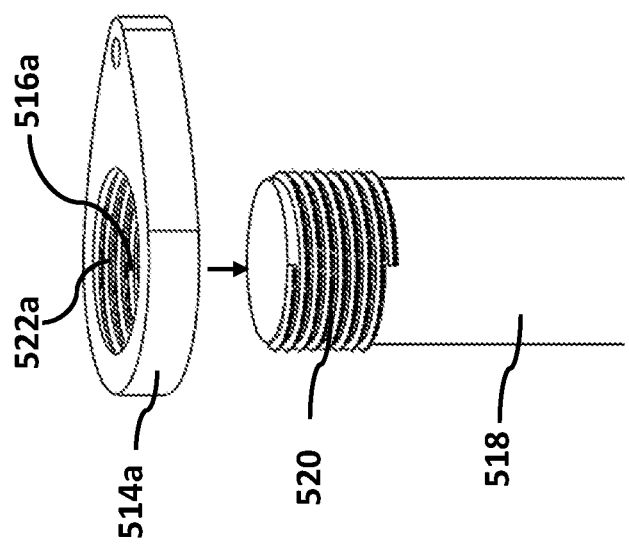

FIG. 9 illustrates an invention embodiment where the proximal end 520 of elongate shaft 518 is provided with screw threads on an external surface that are sized to cooperatively engage with screw threads 522a provided on an internal periphery of any of apertures 516a to 516d of at least one (and in an embodiment all) of constraining member(s) 514a to 514d. The cooperative screw threads ensure that elongate shaft 518 can only be withdrawn through one or more of constraining members 516a to 516d by a deliberate rotational motion imparted to a distal end of elongate shaft 518—and which ensures that the retaining component 502 cannot be accidentally released from its engagement with elongate shaft 518.

Figure 10:
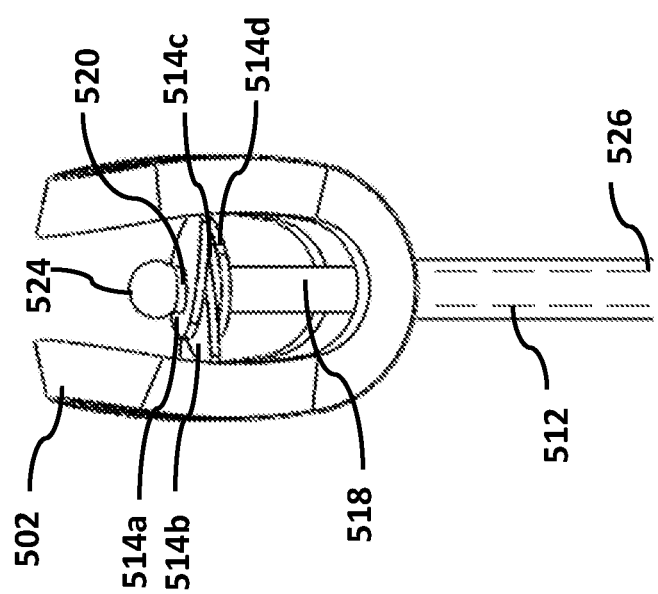
Figure 11:
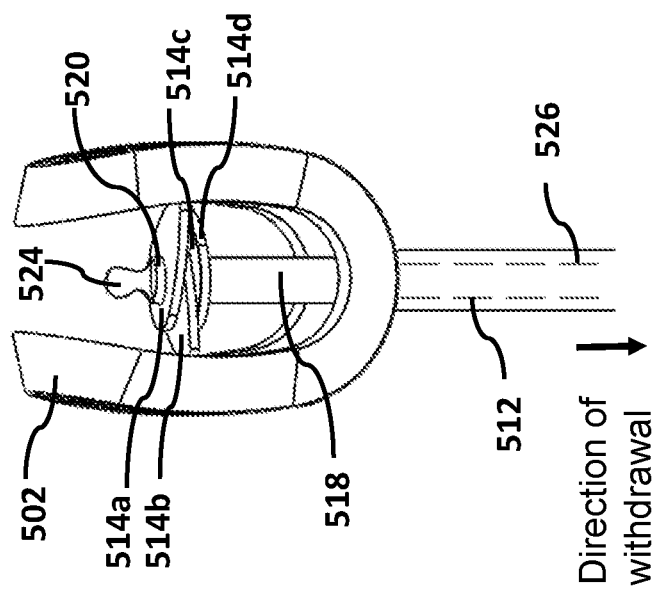

In another embodiment illustrated in FIGS. 10 to 12, the proximal end 520 of elongate shaft 518 is provided with an inflatable or deflatable balloon or stent member 524 configured such that (i) in an inflated state the balloon or stent member 524 resists withdrawal of the elongate shaft 518 through apertures 516a to 516d of constraining members 514a to 514d and (ii) in a deflated state the balloon or stent member 524 permits withdrawal of the elongate shaft 518 through apertures 516a to 516d of constraining members 514a to 514d. This may be achieved by providing an inflatable balloon 524 such that in an inflated state, the horizontal diameter or profile of the inflated balloon 524 is larger than a diameter of at least one of the apertures 516a to 516d (preferably at least aperture 516a within constraining member 514a that, when elongate shaft 518 is positioned within apertures 516a to 516d, is located closest to distal end 526 of elongate shaft 518) and which inflated balloon 524 prevents inadvertent withdrawal of elongate shaft 518 out of apertures 516a to 516d once the elongate shaft 518 has been positioned within said apertures 516a to 516d. On deflation of balloon 524, the horizontal diameter or profile of the balloon is less than the respective diameters of each of apertures 516a to 516d—thereby enabling the elongate shaft 518 to be completely withdrawn from apertures 516a to 516d of constraining members 514a to 514d.

A balloon embodiment is shown in FIG. 10, wherein the inflatable balloon 524 ensures that elongate shaft 518 can only be withdrawn through one or more of constraining members 516a to 516d by a deliberate deflation of said balloon 524—and which ensures that the retaining component 502 cannot be accidentally released from its engagement with elongate shaft 518.

As shown in FIGS. 11 and 12, once the balloon member 524 is deflated, the distal end of elongate shaft 518 is withdrawn through apertures 516a to 516d of constraining members 514a to 514d, to release collapsed retaining component 502 from its engagement with elongate shaft 518, thereby permitting said retaining component 502 to assume its expanded configuration within the subject's rectum, while the elongate shaft 518 is withdrawn from the subject's rectum through the anal opening.

Figure 13:
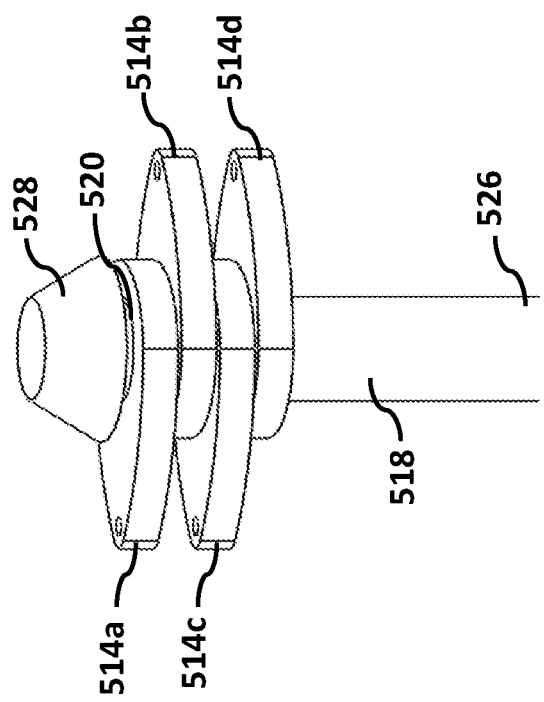
Figure 14:
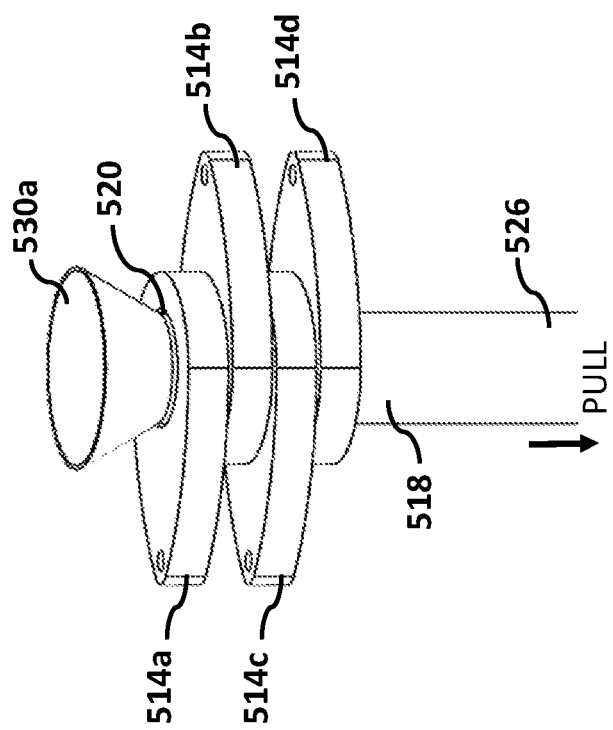
Figure 15A:
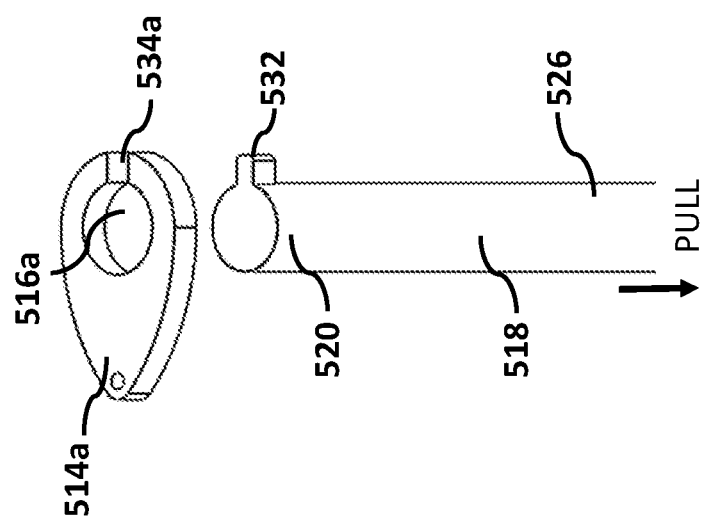
Figure 15B:
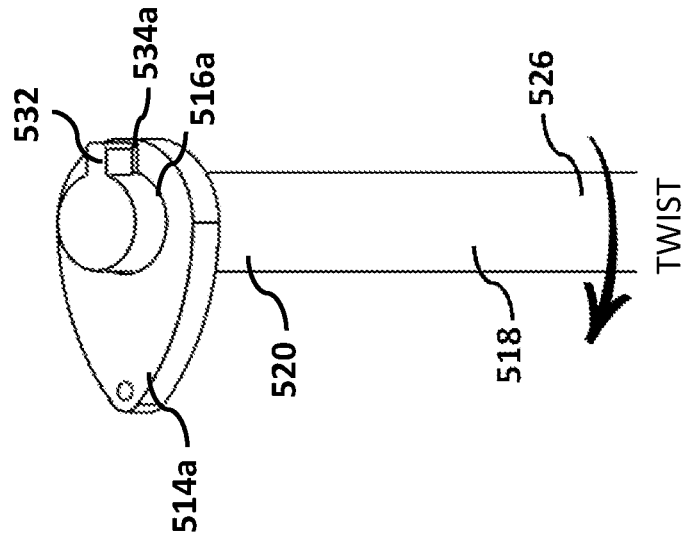
Figure 15C:
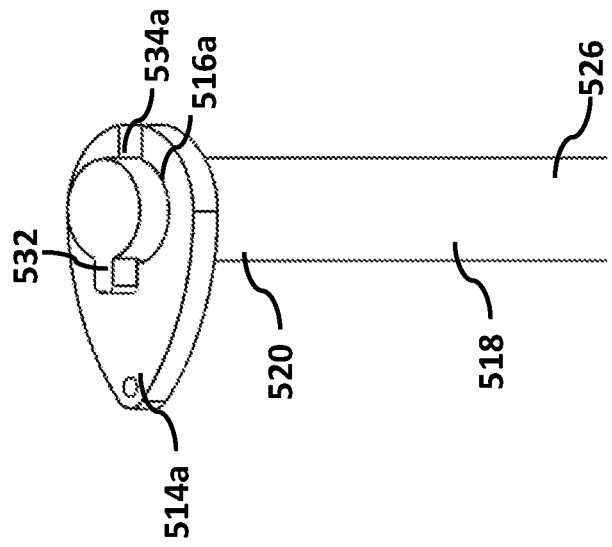

It will be understood that constraining members 514a to 514d and elongate shaft 518 may be configured in any number of other different ways to provide mechanisms that resist or prevent accidental withdrawal of elongate shaft 518 out of apertures 516a to 516d of constraining members 514a to 514d. Exemplary mechanisms may include:

(i) the embodiment illustrated in FIG. 13, wherein a frangible tip 528 is affixed to a proximal end 520 of elongate shaft 518, said frangible tip 528 having a profile that is larger than a diameter of at least one of the apertures 516a to 516d (preferably at least aperture 516a within constraining member 514a that, when elongate shaft 518 is positioned within apertures 516a to 516d, is located closest to distal end 526 of elongate shaft 518) and which frangible tip 528 prevents inadvertent withdrawal of elongate shaft 518 out of apertures 516a to 516d once the elongate shaft 518 has been positioned within said apertures 516a to 516d. Frangible tip 526 may be caused to detach from elongate shaft 518, upon application of more than a predetermined amount of withdrawing force applied to distal end 526 of elongate shaft 518 in a direction away from the subject's rectum, thereby allowing said elongate shaft 518 to be withdrawn out of apertures 516a to 516d, or (ii) the embodiment illustrated in FIG. 14, comprising a compressible tip 530 affixed to a proximal end 520 of elongate shaft 518 and having a profile which, when uncompressed, is larger than an aperture of at least one of the apertures 516a to 516d (preferably at least aperture 516a within constraining member 514a that, when elongate shaft 518 is positioned within apertures 516a to 516d, is located closest to distal end 526 of elongate shaft 518) so as to prevent inadvertent withdrawal of elongate shaft 518 out of apertures 516a to 516d once the elongate shaft has been positioned within said apertures 516a to 516d—and which compressible tip can be forced into a compressed configuration by action of constraining members 514a to 514d as it is withdrawn by application of distally directed force to elongate shaft 518, through apertures 516a to 516d. Importantly, in absence of the distally directed force, the resilient properties of the compressible tip 530 are sufficient to urge said compressible tip 530 to a profile that is substantially larger than a diameter of one or more of apertures 516a to 516d—thereby preventing accidental or inadvertent withdrawal of elongate shaft 518 from apertures 516a to 516d, or (iii) the embodiment illustrated in FIGS. 15A to 15C, comprising at least one latching (in in certain embodiments more than one) protrusion or flange 532 provided at a proximal end 520 of elongate shaft 518—and wherein at least one constraining member 514a (and preferably all constraining members 514a to 514d) has an aperture 516a that is configured to include a correspondingly shaped recess 534a to enable passage of the latching protrusion 532 therethrough (see for example FIG. 15B) when the latching flange 532 is aligned with said recess 534a, and to resist passage of the latching protrusion 532 therethrough when the latching flange 532 is not aligned with said recess (see for example FIG. 15C)—thereby preventing inadvertent withdrawal of elongate shaft 518 out of apertures 516a to 516d unless the elongate shaft has been rotated such that the latching protrusion is aligned with the corresponding recess in the one or more apertures 516a to 516d. As shown in FIG. 15B, elongate shaft 518 may be threaded through one constraining member 514a (and likewise through each of the other constraining members 514b to 514d) by aligning the latching protrusion 532 with the corresponding recess 534a and passing elongate shaft 518 and latching protrusion 532 through aperture 516a of constraining member 514a, and thereafter twisting or rotating elongate shaft 518 (for example, by application of a twisting or rotating force to distal end 526 of elongate shaft 518) and causing latching protrusion 532 to be out of alignment with recess 534a of aperture 514a (as shown in FIG. 15C)—in which state, elongate shaft 518 will be prevented from being withdrawn from constraining member 514a. Thereafter, to withdraw elongate shaft 518 from constraining member 514a, said elongate shaft 518 may be twisted or rotated (for example, by application of a twisting or rotating force to distal end 526 of elongate shaft 518) until latching protrusion 532 is in alignment with recess 534a of aperture 514a (as shown in FIG. 15B)—in which state, elongate shaft 518 may be withdrawn from constraining member 514a (and likewise from the remaining constraining members 514b to 514d so as to release the expansile retaining component 200 from its compressed engagement with elongate shaft 518).

In another embodiment, the constraining members may comprise releasable clips or hooks that may be located on a periphery of retaining component 502 and that hold said retaining component 502 in a collapsed configuration in engagement with elongate shaft 518, or that may be located on elongate shaft 518 and that hold said retaining component 502 in a collapsed configuration in engagement with elongate shaft 518, until manipulation of a distal end of said elongate shaft 518 results in retaining component 518 being released from its collapsed engagement against elongate shaft 518—and is permitted to expand into its expanded configuration.

In various embodiments, constraining members 514a to 514d may be located, sized and configured so as to ensure that the collapsed configuration in which retaining component 502 is releasably retained against elongate shaft 518 is one of the configurations illustrated in FIG. 2B or 2C. In certain embodiments, retaining component 502 is releasably retained against elongate shaft 518 such that elongate shaft 518 passes through the lumen defined by an internal periphery of retaining component 502 (or in other words, elongate shaft 518 is surrounded by retaining component 502 in its collapsed configuration). In another embodiment, retaining component 502 is releasably retained against elongate shaft 518 such that elongate shaft 518 is positioned alongside retaining component 502 in its collapsed configuration.

It will be noted that as a result of the retaining component 502 being releasably constrained in a collapsed configuration against elongate shaft 518, the insertion component need not comprise a hollow outer sheath having an internal diameter sufficient to surround to retaining component 502 in its collapsed configuration, and instead said insertion component may comprise elongate shaft 518 having an external diameter that is less than and preferably significantly less that the diameter or width of retaining component 502 in its collapsed configuration—thereby providing for easier insertion and withdrawal from the anal opening, and for an improved patient experience.

The invention additionally provides a kit for fecal management comprising the device for collection of fecal discharge and the insertion component respectively as discussed in connection with the embodiments above.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclose herein suitably may be practiced in the absence of any element which is not specifically disclosed herein—and in a particular embodiment that is specifically contemplated, the invention is intended to be practiced in the absence of any one or more element which are not specifically disclosed herein.

What is claimed is:

1. An apparatus for fecal management, comprising:
 a device for collection of fecal discharge comprising an expansile retaining component configured for deployment within a subject's rectum and having an annular cross-section, said annular cross-section of the retaining component forming a fluid inlet into an open end of a collection component affixed to said retaining component and forming a receptacle for matter discharged from a subject's rectum, and
 an insertion component for rectal insertion of the retaining component, said insertion component comprising an elongate shaft having a first end positioned proximal to the retaining component and a second end positioned distal to the retaining component;
 wherein at least one of the retaining component and the elongate shaft are provided with a plurality of constraining members configured to releasably constrain the retaining component in a collapsed configuration against an external surface of the elongate shaft.

2. The apparatus as claimed in claim 1, configured such that responsive to release of the elongate shaft from engagement with the retaining component, expansile properties of the retaining component urge the retaining component into an expanded annular configuration.

3. The apparatus as claimed in claim 1, wherein:
 the plurality of constraining members are located on the retaining component; and
 each of the plurality of constraining members comprises a fastening collar having an aperture provided therethrough, wherein said aperture is configured to permit a segment of the elongate shaft to be withdrawably positioned within said fastening collar.

4. The apparatus as claimed in claim 3 wherein the plurality of fastening collars are located along a periphery of the retaining component, such that aligning the apertures that respectively correspond to each constraining member vertically around a single longitudinal axis forces the retaining component into a collapsed configuration.

5. The apparatus as claimed in claim 4, wherein the elongate shaft is withdrawably positioned within the apertures corresponding to the plurality of constraining members to hold the plurality of constraining members in a configuration wherein said apertures are vertically aligned around a single longitudinal axis.

6. The apparatus as claimed in claim 1, wherein an external diameter of the elongate shaft at a portion that is in releasable engagement with the retaining component is less than an external diameter of the retaining component in the collapsed configuration.

7. The apparatus as claimed in claim 1, wherein the plurality of constraining members are located on the elongate shaft and are configured to releasably retain the retaining component in a collapsed configuration against the external surface of the elongate shaft.

8. The apparatus as claimed in claim 1, wherein the plurality of constraining members includes at least one first reciprocal constraining member, provided on one of the elongate shaft and the retaining component, that releasably engages with at least one second reciprocal constraining member on the other of the elongate shaft and the retaining component to releasably retain the retaining component in a collapsed configuration against the external surface of the elongate shaft.

9. The apparatus as claimed in claim 1 wherein the elongate shaft is releasable from engagement with the retaining component by withdrawal of the second end of said elongate shaft in a direction distal to the retaining component.

10. The apparatus as claimed in claim 1, wherein the first end of said elongate shaft is provided with a protrusion that prevents inadvertent release of engagement between the elongate shaft and the retaining component.

11. A kit for fecal management, comprising:
 a device for collection of fecal discharge comprising an expansile retaining component configured for deployment within a subject's rectum and having an annular cross-section, said annular cross-section of the retaining component forming a fluid inlet into an open end of a collection component affixed to said retaining component and forming a receptacle for matter discharged from a subject's rectum, and
 an insertion component for rectal insertion of the retaining component, said insertion component comprising an elongate shaft having a first end configured for positioning proximal to the retaining component and a second end configured for positioning distal to the retaining component;
 wherein at least one of the retaining component and the elongate shaft are provided with a plurality of constraining members configured to releasably constrain the retaining component in a collapsed configuration against an external surface of the elongate shaft.

* * * * *